United States Patent
Okazaki et al.

(10) Patent No.: US 10,575,823 B2
(45) Date of Patent: Mar. 3, 2020

(54) MEDICAL DIAGNOSTIC APPARATUS, MEDICAL IMAGE PROCESSING APPARATUS AND MEDICAL IMAGE PROCESSING METHOD

(71) Applicant: Toshiba Medical Systems Corporation, Otawara-shi (JP)

(72) Inventors: Tomoya Okazaki, Kawasaki (JP); Yukinobu Sakata, Kawasaki (JP); Tomoyuki Takeguchi, Kawasaki (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/869,007

(22) Filed: Sep. 29, 2015

(65) Prior Publication Data
US 2016/0093095 A1    Mar. 31, 2016

(30) Foreign Application Priority Data
Sep. 30, 2014   (JP) ................................ 2014-202041

(51) Int. Cl.
*G06T 15/08* (2011.01)
*A61B 8/00* (2006.01)
(Continued)

(52) U.S. Cl.
CPC ............ *A61B 8/466* (2013.01); *A61B 8/0883* (2013.01); *A61B 8/483* (2013.01); *A61B 8/488* (2013.01);
(Continued)

(58) Field of Classification Search
USPC .......................................... 345/419; 600/438
See application file for complete search history.

(56) References Cited

U.S. PATENT DOCUMENTS 5,797,844 A    8/1998 Yoshioka et al.
8,057,394 B2 *  11/2011 Dala-Krishna ...... A61B 8/0883
                                                         600/437
(Continued)

FOREIGN PATENT DOCUMENTS

JP         9-131345 A    5/1997
JP      2009-78122 A     4/2009
(Continued)

OTHER PUBLICATIONS

Siew Yen Ho "Structure and anatomy of the aortic root", published 2009.*
(Continued)

*Primary Examiner* — Kimbinh T Nguyen
(74) *Attorney, Agent, or Firm* — Oblon, McClelland, Maier & Neustadt, L.L.P.

(57) ABSTRACT

A medical diagnostic apparatus according to one embodiment comprises processing circuitry. The processing circuitry is configured to acquire a three-dimensional shape of a first part based on a contour of the first part in each of a plurality of sectional images intersecting each other along an extending direction of the first part connecting to a cardiac chamber; acquire a three-dimensional shape of a second part, based on a contour of the second part in a sectional image along an extending direction of the second part connecting to the cardiac chamber; and generate a three-dimensional image representing at least some of the first part, the second part, and the cardiac chamber using a three-dimensional shape representing the cardiac chamber and the three-dimensional shapes of the first part and the second part acquired.

24 Claims, 10 Drawing Sheets

(51) Int. Cl.
*G06T 17/20* (2006.01)
*G06T 19/00* (2011.01)
*A61B 8/08* (2006.01)

(52) U.S. Cl.
CPC .......... *A61B 8/5207* (2013.01); *A61B 8/5253* (2013.01); *G06T 17/20* (2013.01); *G06T 19/00* (2013.01); *G06T 2210/41* (2013.01)

(56) References Cited

U.S. PATENT DOCUMENTS

| | | | | |
|---|---|---|---|---|
| 8,328,724 | B2* | 12/2012 | Sengupta | A61B 5/0275 600/437 |
| 8,331,638 | B2* | 12/2012 | Maier | G06T 11/008 382/128 |
| 8,622,915 | B2* | 1/2014 | Dala-Krishna | A61B 8/0883 600/466 |
| 9,196,092 | B2* | 11/2015 | McDermott | G06T 15/08 |
| 2007/0165952 | A1 | 7/2007 | Goto | |
| 2009/0060306 | A1 | 3/2009 | Ohuchi et al. | |
| 2009/0148018 | A1* | 6/2009 | Averkiou | A61B 8/0883 382/131 |
| 2012/0245465 | A1* | 9/2012 | Hansegard | A61B 8/466 600/443 |
| 2012/0296209 | A1* | 11/2012 | Tanaka | A61B 8/0883 600/438 |
| 2013/0127845 | A1* | 5/2013 | Schauf | A61B 8/4488 345/419 |
| 2013/0150719 | A1* | 6/2013 | Orderud | G06T 15/08 600/443 |
| 2013/0211256 | A1* | 8/2013 | Russell | A61B 5/02028 600/438 |
| 2013/0231564 | A1* | 9/2013 | Zagorchev | A61B 8/0883 600/447 |
| 2013/0245441 | A1* | 9/2013 | Datta | A61B 8/13 600/438 |
| 2015/0035829 | A1* | 2/2015 | Miyamoto | A61B 5/055 345/423 |
| 2015/0305707 | A1 | 10/2015 | Okazaki et al. | |
| 2016/0093044 | A1 | 3/2016 | Okazaki et al. | |
| 2016/0140707 | A1 | 5/2016 | Abe et al. | |
| 2017/0100144 | A1* | 4/2017 | Zhadkevich | A61B 17/12045 |

FOREIGN PATENT DOCUMENTS

| | | |
|---|---|---|
| JP | 5276407 B2 | 8/2013 |
| JP | 2015-213745 A | 12/2015 |
| JP | 2016-67559 A | 5/2016 |
| JP | 2016-101482 A | 6/2016 |
| WO | WO 2005/058165 A1 | 6/2005 |

OTHER PUBLICATIONS

T. F. Cootes, et al., "Active Shape Models—Their Training and Application" Computer Vision and Image Understanding, vol. 61, No. 1, Jan. 1995, pp. 38-59.

* cited by examiner

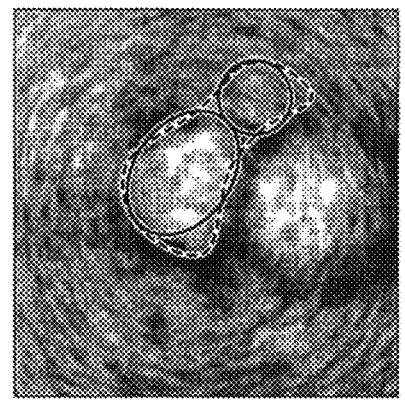
F I G. 10A
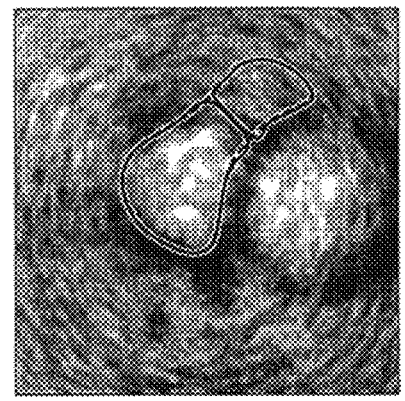
F I G. 10B

MEDICAL DIAGNOSTIC APPARATUS, MEDICAL IMAGE PROCESSING APPARATUS AND MEDICAL IMAGE PROCESSING METHOD

CROSS-REFERENCE TO RELATED APPLICATIONS

This application is based upon and claims the benefit of priority from the Japanese Patent Application No. 2014-202041, Sep. 30, 2014, the entire contents of all of which are incorporated herein by reference.

FIELD

This embodiment relates to an ultrasonic diagnostic apparatus, an ultrasonic image processing apparatus and an ultrasonic image processing method that provides information effective for medical diagnosis by outputting local motion information of tissue such as myocardium (a muscle configuring a heart) using an ultrasonic image.

BACKGROUND

An ultrasonic diagnostic apparatus can display a pulsation of a heart and a state of a fetus' motion in real time with a simple operation by bringing an ultrasonic probe into contact with a body surface, and further, has a high safety and thus, it is possible to repeatedly perform examinations. Besides, the ultrasonic diagnostic apparatus has a small system scale as compared to another diagnostic equipment using such as X-ray, computerized tomography (CT) and magnetic resonance imaging (MRI), and is capable of easily performing examination by being moved to a bedside, which can be referred to as a convenient diagnosis method. Although there are various types of ultrasonic diagnostic apparatuses to be used in such an ultrasonic diagnosis depending on types of functions provided in the respective apparatuses, and among them, a small apparatus having a size that can be carried with one hand has been developed, and the ultrasonic diagnosis does not cause exposure to radiation unlike the X-ray and the like, and thus, can be used in obstetrics, home medical care and the like.

Recently, there is a tissue tracking imaging (TTI) method as a method of evaluating a function of an object as biological tissue in objective and quantitative manner using such an ultrasonic diagnostic apparatus. According to the TTI method, it is possible to provide a quantitative evaluation method by a local wall motion index such as a strain and displacement using tissue velocity. In the TTI method, it is necessary to input a three-dimensional boundary of the object in volume data for a reference temporal phase. As such an input method, a technique has been known in which a plurality of sectional images are set to the volume data, a boundary of the object is traced on each two-dimensional image corresponding to each section, and the three-dimensional boundary is generated by an interpolation process among the sections. In this technique, for example, in a case where a three-dimensional boundary of an object, which is myocardium of a left ventricle of a heart to be included in an ultrasonic image, is input to volume data of a reference temporal phase, a myocardial boundary is traced in a plurality of short-axis sections of the left ventricle, and then a three-dimensional myocardial boundary is generated by the interpolation process among each sections. If targets to be used for analysis are only a ventricle and an inflow section for flowing blood into the ventricle (for example, a mitral valve in the case of the left ventricle, and a tricuspid valve in the case of a right ventricle), the both are relatively clearly displayed with only using the short-axis section in the related art by setting a position of an ultrasonic probe in accordance with an axis passing through the ventricle and the inflow section, and it is easy to suitably set the myocardial boundary.

However, in a case where the targets to be used for the analysis also include an outflow section for flowing the blood out from the ventricle (for example, a pulmonary valve in the case of the right ventricle) in addition to the ventricle and the inflow section, it is possible to sufficiently secure visibility of the ventricle and one of the inflow section or the outflow section, but it is difficult to sufficiently secure visibility of the other. As a result, the time required for the analysis and the diagnosis increases. In addition, it is difficult to suitably set the myocardial boundary, and thus, it is difficult to sufficiently secure accuracy in the analysis and the diagnosis.

From a viewpoint of the above-described situation, an object is to provide an ultrasonic diagnostic apparatus, an ultrasonic image processing apparatus and an ultrasonic image processing program capable of reducing time required for analysis and diagnosis, and further, improving accuracy in the analysis and the diagnosis.

BRIEF DESCRIPTION OF THE DRAWINGS

FIGS. 10A and 10B are diagrams for describing a process of deforming an elliptical shape and a circular shape on a sectional image linked to the ventricle such that three-dimensional shapes of an inflow section and an outflow section are smoothly connected to each other.

DETAILED DESCRIPTION

Figure 1:
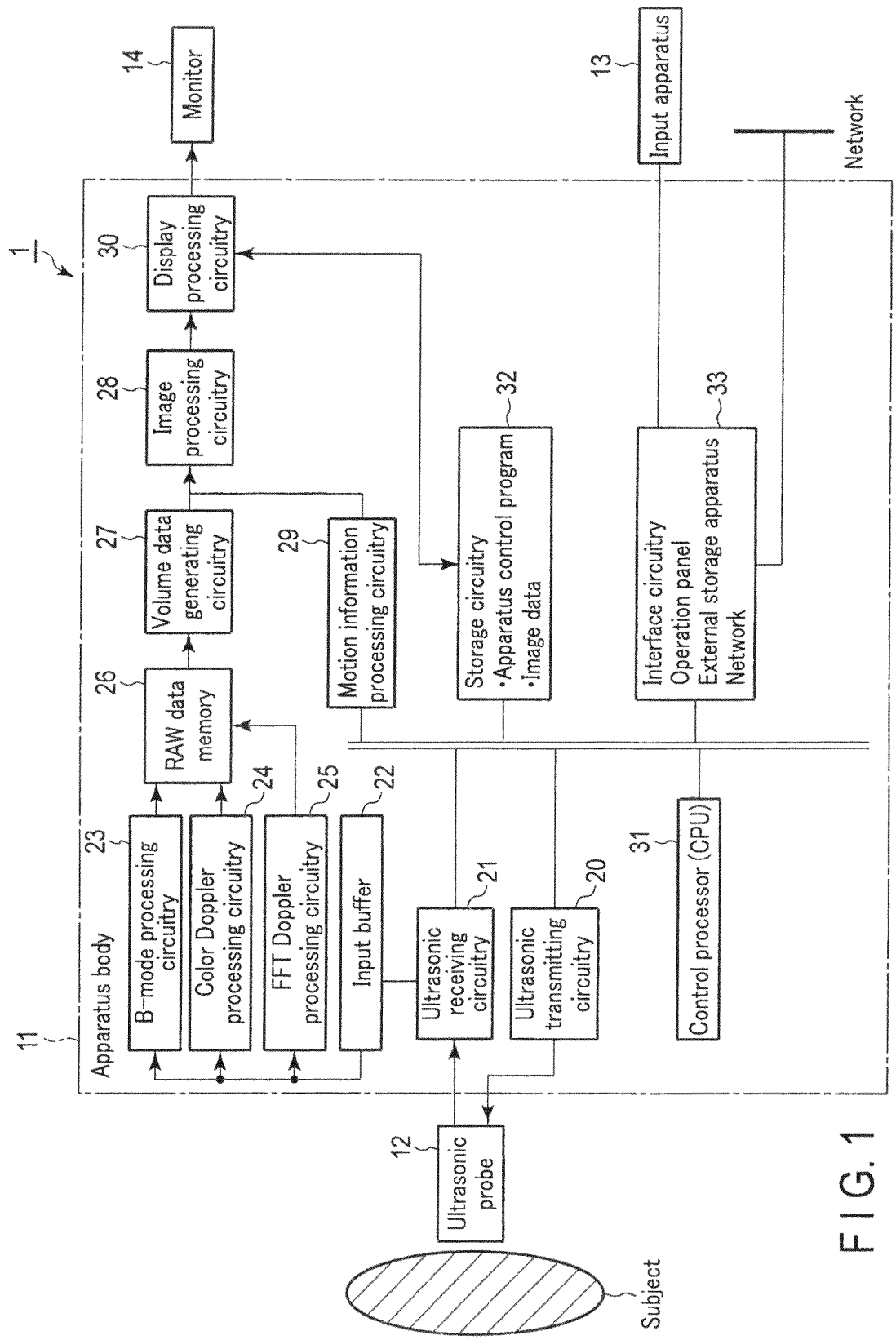
FIG. 1 is a block diagram illustrating a configuration of an ultrasonic diagnostic apparatus according to an embodiment.

A medical diagnostic apparatus according to one embodiment comprises processing circuitry. The processing circuitry is configured to acquire a three-dimensional shape of a first part based on a contour of the first part in each of a plurality of sectional images intersecting each other along an extending direction of the first part connecting to a cardiac chamber; acquire a three-dimensional shape of a second part, based on a contour of the second part in a sectional image along an extending direction of the second part connecting to the cardiac chamber; and generate a three-dimensional image representing at least some of the first part, the second part, and the cardiac chamber using a three-dimensional shape representing the cardiac chamber and the three-dimensional shapes of the first part and the second part acquired.

Hereinafter, an embodiment will be described in accordance with the drawings. Incidentally, in the following description, components having substantially the same function and configuration will be attached with the same reference numerals and an overlapped description thereof will be made only in a necessary case.

FIG. 1 is a block diagram illustrating a configuration of an ultrasonic diagnostic apparatus according to an embodiment; As illustrated in FIG. 1, an ultrasonic diagnostic apparatus 1 is provided with an ultrasonic probe 12, an input apparatus 13, a monitor 14, an ultrasonic transmitting circuitry 20, an ultrasonic receiving circuitry 21, an input buffer 22, a B-mode processing circuitry 23, a color Doppler processing circuitry 24, an FFT Doppler processing circuitry 25, a RAW data memory 26, a volume data generating circuitry 27, a motion information processing circuitry 29, an image processing circuitry 28, a display processing circuitry 30, a control processor (CPU) 31, a storage circuitry 32 and an interface circuitry 33. Hereinafter, a description will be made regarding a function of individual component. Incidentally, a data acquisition unit is configured by the ultrasonic probe 12, the input apparatus 13, the monitor 14, the ultrasonic transmitting circuitry 20, the ultrasonic receiving circuitry 21, the input buffer 22, the B-mode processing circuitry 23, the color Doppler processing circuitry 24, the FFT Doppler processing circuitry 25, the RAW data memory 26 and the volume data generating circuitry 27.

The ultrasonic probe 12 is a device (probe) that transmits an ultrasonic wave with respect to a subject having a living body as a typical example, and receives a reflected wave from the subject based on the transmission ultrasonic wave, and has an array of a plurality of a plurality of piezoelectric vibrators (ultrasonic transducers), a matching layer, a backing material and the like at a distal end thereof. The piezoelectric vibrator transmits an ultrasonic wave to a desired direction in a scan region based on a driving signal from the ultrasonic transmitting circuitry 20, and converts the reflected wave from the subject into an electrical signal. The matching layer is an intermediate layer that is provided in the piezoelectric vibrator and causes ultrasonic energy to be propagated with high efficiency. The backing material prevents propagation of the ultrasonic wave from the piezoelectric vibrator to a rear side. When the ultrasonic wave is transmitted from the ultrasonic probe 12 to the subject, the transmitted ultrasonic wave is sequentially reflected by a discontinuity surface of acoustic impedance of internal body tissue, and is received by the ultrasonic probe 12 as an echo signal. The amplitude of the echo signal depends on a difference in the acoustic impedance in the reflecting discontinuity surface. In addition, an echo in a case where an ultrasonic pulse is reflected by a moving blood flow depends on a velocity component of an ultrasonic transmitting and receiving direction of a moving object due to the Doppler effect, and is subjected to a frequency shift. In the embodiment, the ultrasonic probe 12 is configured to be capable of acquiring volume data, and to be a two-dimensional array probe (probe in which plurality of ultrasonic vibrators are arranged in a two-dimensional matrix form) or a mechanical 4D probe (probe capable of performing the ultrasonic scan while mechanically swinging the ultrasonic vibrator array in a direction perpendicular to the array direction).

The input apparatus 13 is connected to an apparatus body 11, and has various types of switches, buttons, a trackball, a mouse, a keyboard and the like which are used to input, to the apparatus body 11, various types of instructions, conditions, an instruction to set a region of interest (ROI), various types of image quality condition setting instructions, and the like from an operator such as selection of an imaging mode.

The monitor 14 displays morphological information in a living body and blood flow information acquired through a color Doppler mode as images based on video signals from the display processing circuitry 30. In addition, the monitor 14 displays an ultrasonic image to be reproduced by a color Doppler imaging method, which will be described later, in a predetermined form together with a predetermined information.

The ultrasonic transmitting circuitry 20 has a trigger generation circuit, a delay circuit, and a pulser circuit (which are not illustrated). The trigger generation circuit repetitively generates trigger pulses for the formation of transmission ultrasonic waves at a predetermined rate frequency fr Hz (period: 1/fr sec). In addition, in the delay circuit, a delay time necessary to focus an ultrasonic wave into a beam and determine transmission directivity for each channel is given to each trigger pulse. The pulser circuit applies a driving pulse to the probe 12 at the timing based on this trigger pulse. In addition, the ultrasonic transmitting circuitry 20 performs ultrasonic transmission, which will be described later, based on a control signal from the control processor 31 in a color Doppler imaging process.

The ultrasonic receiving circuitry 21 has an amplification circuit, an A/D converter, the delay circuit, an adder, a quadrature detection circuit, and the like (which are not illustrated). The amplification circuit amplifies the echo signal taken via the probe 12 for each channel. The A/D converter converts the amplified analog echo signal into a digital echo signal. The delay circuit determines reception directivity with respect to the echo signal converted into the digital signal, and gives the delay time necessary for performing reception dynamic focusing, and then the adder performs adding processing is performed. A reflection component from a direction corresponding to the reception directivity of the echo signal is enhanced through the adding processing, and a composite beam for ultrasonic transmission and reception is formed in accordance with the reception directivity and transmission directivity. The quadrature detection circuit converts an output signal of the adder into an in-phase signal (I signal) of a baseband, and a quadrature-phase signal (Q signal). The quadrature detection circuit outputs the I signal and the Q signal (IQ signal), as the echo signal, to a subsequent processing system. Incidentally, the quadrature detection circuit may perform conversion processing into a radio frequency (RF) signal. In addition, the ultrasonic receiving circuitry 21 performs ultrasonic reception, which will be described later, based on the control signal from the control processor 31 in the color Doppler imaging process.

The input buffer 22 is a buffer that temporarily stores the echo signal (the IQ signal or the RF signal) output from the ultrasonic receiving circuitry 21. The input buffer 22 is, for example, a first-in/first-out (FIFO) memory, and temporarily stores the IQ signals for several frames (or the IQ signals corresponding to several volumes). In addition, in a case where the IQ signal for one frame is newly output from the ultrasonic receiving circuitry 21, the input buffer 22 rewrites the IQ signal corresponding to the temporally oldest frame with the IQ signal, which has been newly received from the ultrasonic receiving circuitry 21.

The B-mode processing circuitry 23 receives the echo signal from the input buffer 22, and performs logarithmic amplification, envelope detection processing, and the like for the signal to generate data of which signal intensity is expressed by a brightness level.

The color Doppler processing circuitry 24 performs color Doppler processing using the echo signal received from the input buffer 22, and outputs a power signal and a velocity signal.

The FFT Doppler processing circuitry 25 performs fast Fourier transform using the acquired echo signal in a continuous wave Doppler mode, and outputs a spectrum signal.

The RAW data memory 26 generates B-mode RAW data, which is B-mode data on a three-dimensional ultrasonic scan line, using a plurality of the B-mode data received from the B-mode processing circuitry 23. In addition, the RAW data memory 26 generates blood flow RAW data, which is blood flow data on the three-dimensional ultrasonic scan line, using a plurality of the blood flow data received from the color Doppler processing circuitry 24. Incidentally, it may be configured such that a three-dimensional filter is inserted subsequently to the RAW data memory 26 to perform spatial smoothing for the purpose of reducing noise and improving image concatenation.

The volume data generating circuitry 27 generates B-mode volume data and blood flow volume data by performing RAW-voxel conversion including an interpolation process in which spatial position information is added.

The image processing circuitry 28 performs predetermined image processing such as volume rendering, multi planar reconstruction (MPR), and maximum intensity projection (MIP) for the volume data received from the volume data generating circuitry 27 or the motion information processing circuitry 29. Incidentally, it may be configured such that a two-dimensional filter is inserted subsequently to the image processing circuitry 28 to perform the spatial smoothing for the purpose of reducing the noise and improving the image concatenation.

The motion information processing circuitry 29 performs various types of processes in relation to a tissue tracking imaging method using the B-mode volume data or the blood flow volume data output from the volume data generating circuitry 27. In addition, the motion information processing circuitry 29 performs a process according to a function of supporting setting a three-dimensional myocardial shape of a ventricle (a ventricle three-dimensional myocardial shape setting support process), which will be described later, in the tissue tracking imaging method. A description will be made later in detail regarding a configuration and an operation of the motion information processing circuitry 29.

The display processing circuitry 30 performs various types of processes such as a dynamic range, brightness, contrast, γ curve correction, RGB conversion, and the like for various types of image data generated and processed by the image processing circuitry 28.

The control processor 31 has a function as an information processing apparatus (computer), and controls each operation of the components. In addition, the control processor 31 controls the motion information processing circuitry 29 and the like in the ventricle three-dimensional myocardial shape setting support process which will be described alter.

The storage circuitry 32 stores a program for implementing the tissue tracking imaging method, a program for implementing the ventricle three-dimensional myocardial shape setting support process, which will be described alter, a diagnostic protocol, transmission and reception conditions and other data groups. In addition, the storage circuitry 32 is also used to store images in an image memory (not illustrated) if necessary. It is possible to transfer data in the storage circuitry 32 to an external peripheral apparatus via the interface circuitry 33.

The interface circuitry 33 is an interface in relation to the input apparatus 13, a network, and a new external storage apparatus (not illustrated). It is also possible to connect another apparatus to the ultrasonic diagnostic apparatus body 11 via the interface circuitry 33. In addition, it is possible to transfer data such as the ultrasonic image, analysis results, obtained by the apparatus, to another apparatus via the network by the interface circuitry 33.

(Tissue Tracking Imaging)

Next, a description will be made briefly regarding the tissue tracking imaging (TTI) method which is a technique serving as a premise of the embodiment. According to the tissue tracking imaging method, parameters of local displacement and strain are imaged, as motion information of the tissue, while tracking tissue positions associated with motions. According to the method, it is possible to create and display the images of the local strain and displacement of the myocardium of the heart using, for example, short-axis images, and an analysis on temporal change with respect to a local region of an image output value is supported. More details of the tissue tracking imaging method are described in, for example, Jpn. Pat. Appln. KOKAI Publication No. 2003-175041.

Incidentally, in the tissue tracking imaging method, a spatio-temporal distribution image of the tissue velocity in relation to a plurality of temporal phases (an image representing the velocity of diagnosis target tissue in each position) is required. The spatio-temporal distribution image of the tissue velocity (hereinafter, simply as a "velocity distribution image") is obtained by performing a pattern matching process with respect to a plurality of two-dimensional or three-dimensional tissue images in relation to the plurality of temporal phases collected through the B-mode and the like, or by generating the image using the two-dimensional or three-dimensional ultrasonic images in relation to the plurality of temporal phases collected by a tissue Doppler method. In recent years, such a method based on the pattern matching process has been generally called a speckle tracking method in more cases.

(Motion Information Processing Unit)

The above-described processing in relation to the tissue tracking imaging method (in particular, the tissue tracking imaging method using the ventricle three-dimensional myocardial shape setting support function which will be described later) is performed by the motion information processing circuitry 29.

Figure 2:
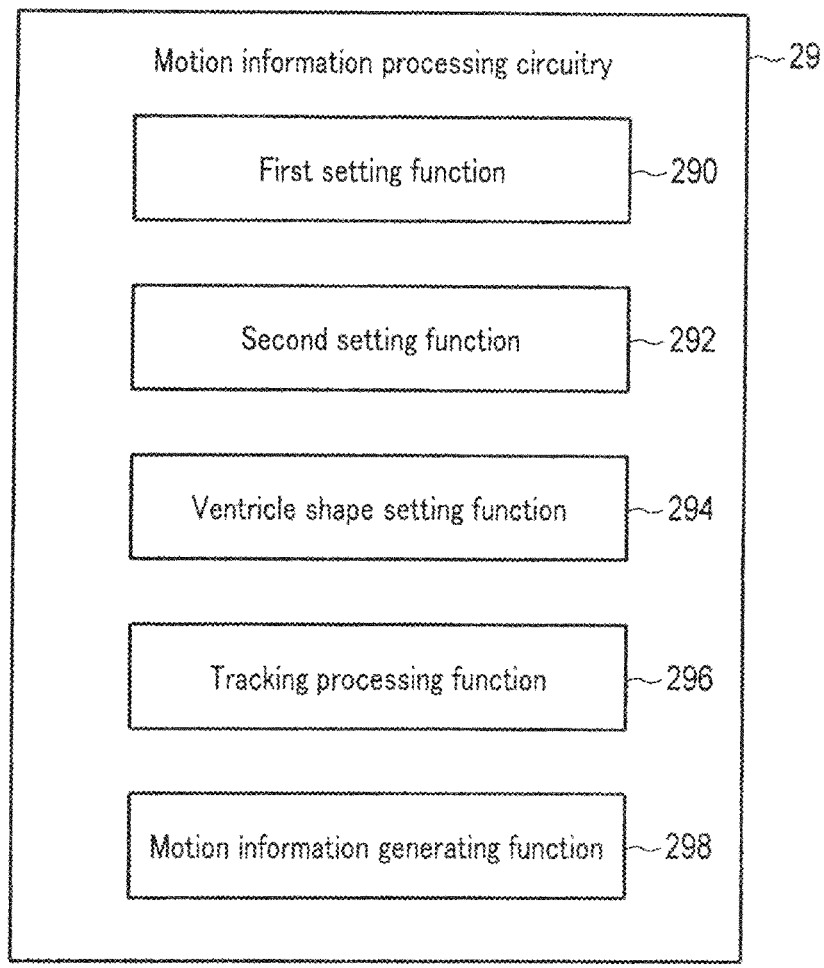
FIG. 2 is a block configuration diagram of a motion information processing circuitry 29 according to the embodiment.

FIG. 2 is a block configuration diagram of the motion information processing circuitry 29. As illustrated in FIG. 2, the motion information processing circuitry 29 has a first setting function 290, a second setting function 292, a ventricle shape setting function 294, a tracking processing function 296, and a motion information generating function 298.

The first setting function 290 sets a three-dimensional shape of a part (first part) for performing inflow of the blood flow to the ventricle with respect to the volume data in relation to the heart, which is generated in the volume data generating circuitry 27, in the ventricle three-dimensional myocardial shape setting support process which will be described later.

The second setting function 292 sets a three-dimensional shape of a part (second part) for performing outflow of the blood flow from the ventricle with respect to the volume data in relation to the heart, which is generated in the volume data generating circuitry 27, in the ventricle three-dimensional myocardial shape setting support process which will be described later.

The ventricle shape setting function 294 sets the three-dimensional myocardial shape of the ventricle including the first part and the second part to the volume data using the three-dimensional shape of the first part and the three-dimensional shape of the second part.

The tracking processing function 296 performs tracking by performing the pattern matching process with respect to a plurality of the volume data in relation to the plurality of temporal phases for each position of target (for example, the ventricle three-dimensional myocardial shape, an axis of the first part, an axis of the second part, and the like) to be set with respect to the volume data in a reference temporal phase (for example, an initial temporal phase), and generates the velocity distribution image for each temporal phase.

The motion information generating function 298 generates motion information (for example, the strain, a strain rate, the displacement, the velocity, twist, a twist rate, and the like) in each position of the myocardium using the generated velocity distribution image for each temporal phase.

(Three-dimensional Myocardial Shape Setting Support Function of Cardiac Chamber)

Next, a description will be made regarding a function of supporting setting a three-dimensional myocardial shape of a cardiac chamber provided in the ultrasonic diagnostic apparatus 10. This function supports setting of the myocardial region including the first part of performing the inflow of the blood, the second part of performing the outflow of the blood, and the cardiac chamber, for example, in a case where myocardial tissue is imaged using the tissue tracking imaging method. Incidentally, hereinafter, the "cardiac chamber" is assumed to be a "right ventricle", the "first part" is assumed to be a "tubular structure (an inflow section) including a tricuspid valve" for causing the blood to flow into the right ventricle, and the "second part" is assumed to be a "tubular section (an outflow section) including a pulmonary valve" for causing the blood to flow out from the right ventricle for the sake of a detailed description. However, there is no intent to limit the "cardiac chamber", the "first part" and the "second part" to the corresponding example, and for example, the "cardiac chamber" may be a "left ventricle", a "right atrium", or a "left atrium", and the "first part" or the "second part" may be a part other than a tubular region.

Figure 3:
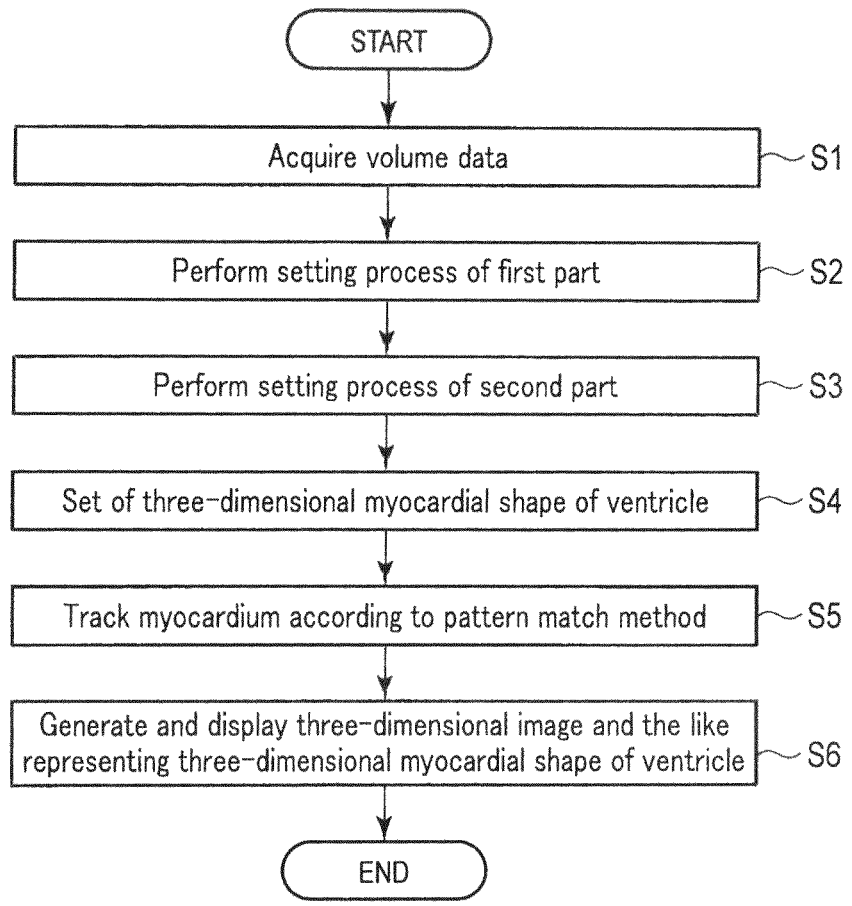
FIG. 3 is an example of a flowchart in a case where tissue tracking imaging is performed using a function of supporting setting a three-dimensional myocardial shape of a ventricle implemented by an ultrasonic diagnostic apparatus 1 according to the embodiment.

FIG. 3 is an example of a flowchart in a case where tissue tracking imaging is performed using a function of supporting setting a three-dimensional myocardial shape of a ventricle implemented by an ultrasonic diagnostic apparatus 1 according to the embodiment; Hereinafter, a description will be made in detail regarding a process performed in each step.

[Acquisition of Volume Data: Step S1]

First, a three-dimensional region including at least the right ventricle is scanned by ultrasonic (scanned according to the B-mode), and the volume data is acquired for each temporal phase for a predetermined period, for example, over one heartbeat or more. Here, the "temporal phase" or a "cardiac phase" indicates an arbitrary one point in time (timing) in a periodic motion of the heart.

Incidentally, in the embodiment, it is configured to acquire the volume data over the plurality of temporal phases in order to exemplify a typical application to the tissue tracking imaging method. However, the ventricle three-dimensional myocardial shape setting support function can be implemented if there is the volume data corresponding to one temporal phase. Accordingly, in this Step S1, it may be configured such that the volume data in one temporal phase corresponding to an end-systole or an end-diastole, for example, if necessary.

[Setting Process of First Part: Step S2]

The first setting function 290 inputs a contour line of the myocardial region of the first part for performing the inflow of the blood to the right ventricle using a section taken along the axis of the first part with respect to the volume data corresponding to a predetermined temporal phase (for example, the initial temporal phase) among the acquired volume data corresponding to the respective temporal phases, and sets the three-dimensional shape approximating the first part by the interpolation process. More details thereof are as follows.

Figure 4A:
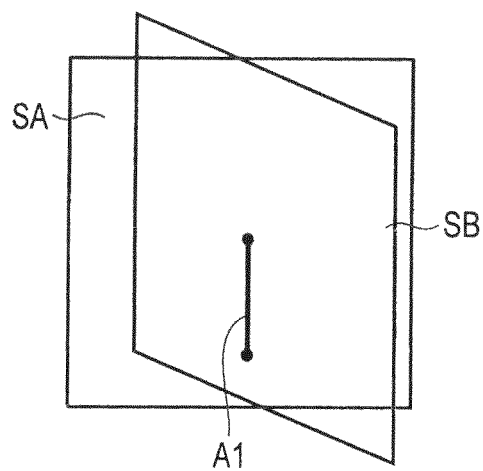
FIGS. 4A and 4B are diagrams for describing a setting process of a first part.

FIGS. 4A to 5C are diagrams for describing a setting process of the first part. When the plurality of volume data over the plurality of temporal phases are acquired in Step S1, the first setting function 290 sets two long-axis sections SA and SB (for example, two orthogonal sections) taken along an axis A1 of the first part (along an extending direction of the first part) with respect to the volume data corresponding to the predetermined temporal phase as illustrated in FIG. 4A. Here, the "extending direction" means a direction along a straight line or an approximate line which connects a center of an inlet and a center of an outlet of a tubular inflow path, for example. In addition, although the example in which the long-axis sections SA and SB are parallel is illustrated using the expression, "along the extending direction of the first part" in the above description, the sections are not bound by this example, and an angle formed between the section and the extending direction of the first part may be within ±20 degree.

The setting of these two long-axis sections SA and SB can be implemented according to a predetermined algorithm, but may be set or fine-tuned by a manual operation. When the two long-axis sections SA and SB taken along the axis A1 of the first part, the image processing circuitry 28 generates long-axis sectional images SAI and SBI which correspond to the long-axis sections SA and SB, respectively. Each of the generated long-axis sectional images SAI and SBI is displayed on the monitor 14 as illustrated in FIG. 4B, for example.

Figure 4B:
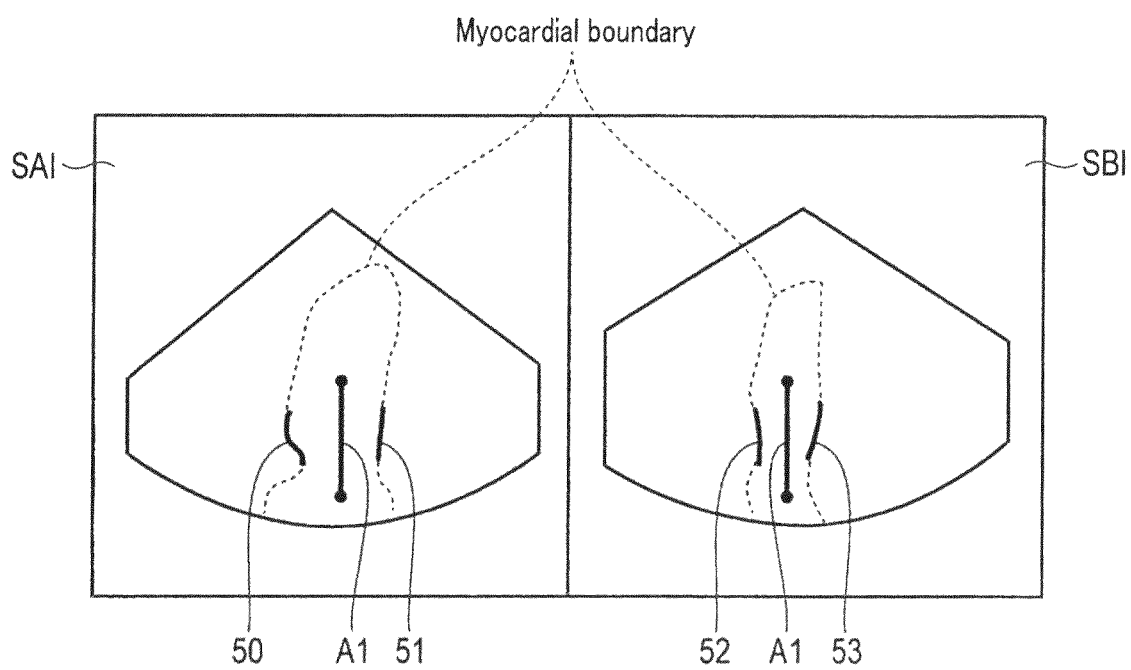

A user traces the contour line of the myocardial region in the first part (the inflow section) with respect to the two long-axis sectional images SAI and SBI, displayed like FIG. 4B, by the input apparatus 13, sets the contour lines 50 and 51 in the long-axis sectional image SAI, and sets the contour lines 52 and 53 in the long-axis sectional image SBI, for example.

Figure 5A:
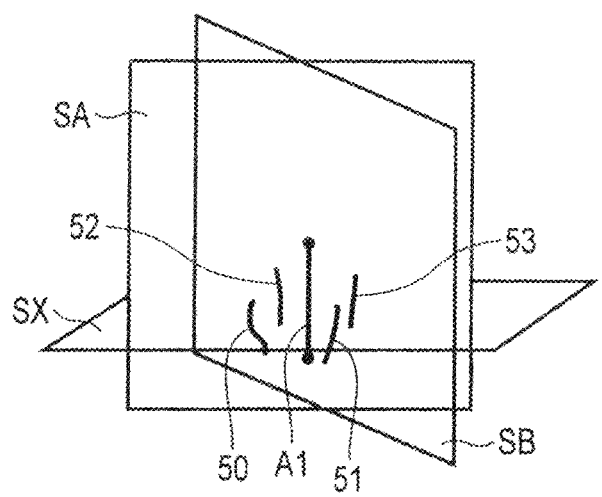
FIGS. 5A to 5C are diagrams for describing the setting process of the first part.
Figure 5B:
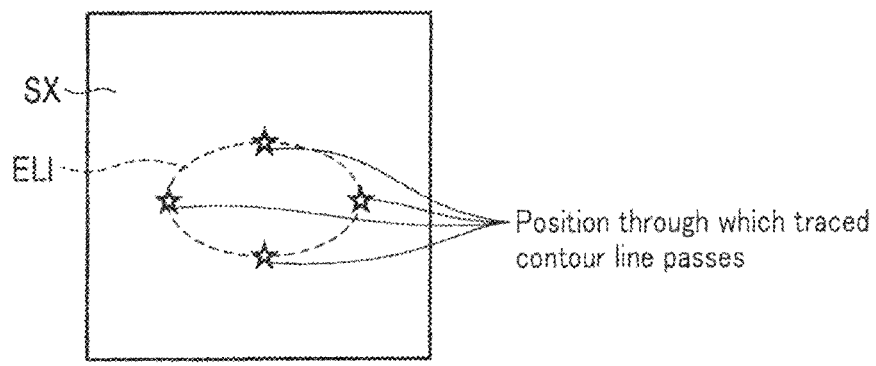
Figure 5C:
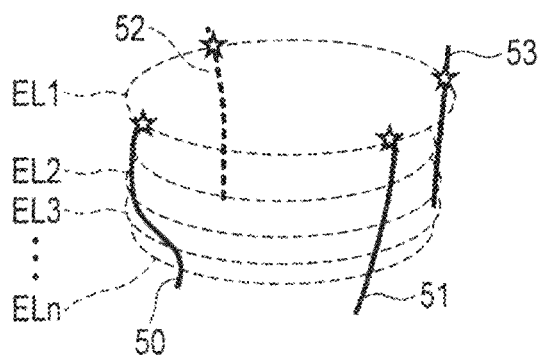

It is possible to explicitly grasp a relationship of spatial positions of the four contour lines 50, 51, 52 and 53 as illustrated in FIG. 5A as a coordinate on the volume data. As illustrated in FIG. 5B, the first setting function 290 sets a short-axis section SX1 which intersects the long-axis sections SA and SB, and approximates a contour of the first part by an ellipse EL1 using four points at which the short-axis section and each of the four contour lines 50, 51, 52 and 53 intersect each other. In the same manner, the first setting function 290 sets short-axis sections SX2, SX3, . . . , SXn each of which intersects the long-axis sections SA and SB, and approximates the contour of the first part by ellipses EL2, EL3, ELn using respective four points at which each of the short-axis sections and each of the four contour lines 50, 51, 52 and 53 intersect each other. The first setting function 290 sets the three-dimensional image approximating the first part to the volume data by performing the interpolation process on a plurality of the ellipses EL2, EL3, . . . , ELn thus obtained. Incidentally, the expression, "intersect" in the above description means any of intersecting at a formed angle therebetween being 70 degree to 110 degree, and more preferably at a formed angle therebetween being 90 degree.

Incidentally, in the above description, a case in which the contour line of the myocardial region in the first part is set using the two long-axis sections SA and SB has been exemplified. However, it is not limited to such an example, and may be configured such that the contour line of the myocardial region in the first part is set using three or more long-axis sections. In addition, the two long-axis sections SA and SB are set to the two orthogonal sections, but are not necessarily orthogonal. Further, the contour line of the myocardial region in each of the long-axis sectional images may be automatically estimated by, for example, an image processing method disclosed in Non Patent Literature 1.

[Setting Process of Second Part: Step S3]

The second setting function 292 inputs a contour line of the myocardial region of the second part for performing the outflow of the blood from the right ventricle by a sectional image taken along the axis of the second part with respect to the volume data corresponding to the predetermined temporal phase, and sets the three-dimensional shape approximating the second part by the interpolation process. More details thereof are as follows.

Figure 6:
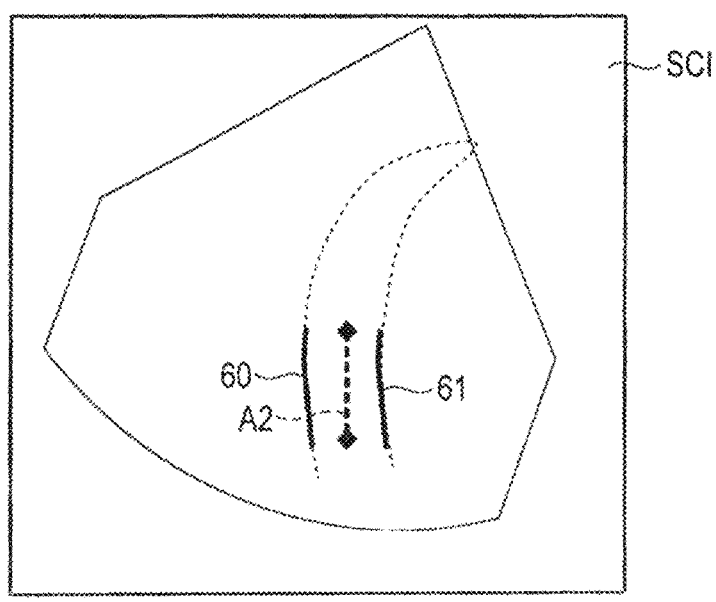
FIG. 6 is a diagram for describing a setting process of a second part.
Figure 7A:
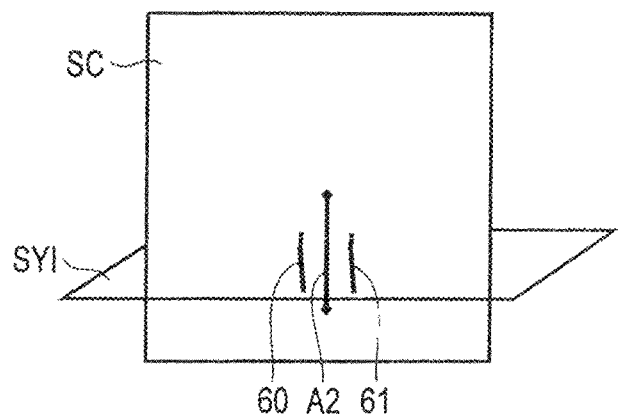
FIGS. 7A to 7C are diagrams for describing the setting process of the second part.
Figure 7B:
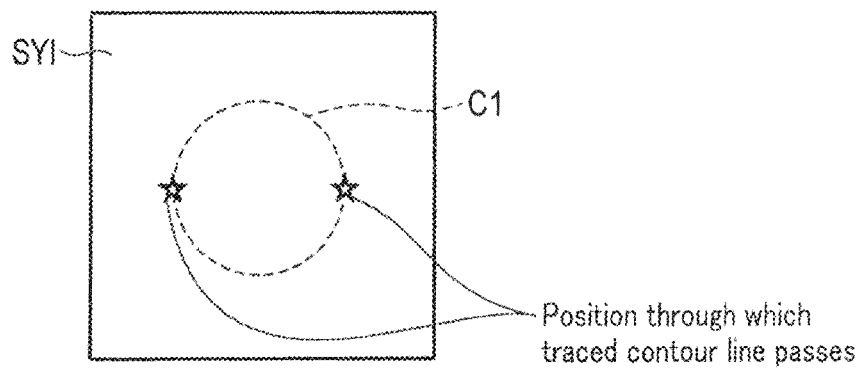
Figure 7C:
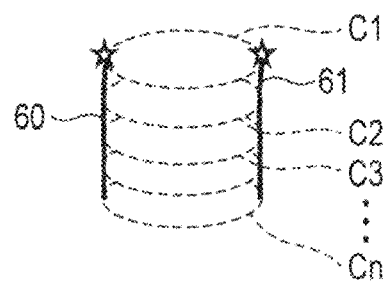

FIGS. 6 to 7C are diagrams for describing a setting process of the second part. The second setting function 292 sets a long-axis section SC taken along an axis A2 of the second part (along an extending direction of the second part) with respect to the volume data corresponding to the predetermined temporal phase. The setting of the long-axis section SC can be implemented according to a predetermined algorithm, but may be set or fine-tuned by a manual operation. When the long-axis section SC taken along the axis A2 of the second part is set, the image processing circuitry 28 generates a long-axis sectional image SCI which corresponds to the long-axis section SC. The generated long-axis sectional image SCI is displayed on the monitor 14 as illustrated in FIG. 6, for example. Incidentally, the expression, "extending direction", "along the extending direction" and the like have the same meaning as described above.

The user traces the contour line of the myocardial region in the second part (the outflow section) with respect to the long-axis sectional image SCI, displayed like FIG. 6, by the input apparatus 13, and sets the contour lines 60 and 61 in the long-axis sectional image SCI.

As illustrated in FIG. 7A, it is possible to explicitly grasp a relationship of spatial positions of the two contour lines 60 and 61 as a coordinate on the volume data. As illustrated in FIG. 7B, the second setting function 292 sets a short-axis section SY1 which intersects the long-axis section SC, and approximates a contour of the second part by a circle C1 using two points at which the short-axis section and each of the two contour lines 60 and 61 intersect each other. In the same manner, the second setting function 292 sets short-axis sections SY2, SY3, . . . , SYn each of which intersects the long-axis section SC, and approximates the contour of the second part by circles C2, C3, . . . , Cn using respective two points at which each of the short-axis sections and each of the two contour lines 60 and 61 intersect each other. The second setting function 292 sets the three-dimensional image approximating the second part to the volume data by performing the interpolation process on a plurality of the circles C2, C3, . . . , Cn thus obtained.

Here, the approximation by the circle is performed using the one long-axis section SC in the setting of the second part as the outflow section while the elliptical approximation is performed using the two long-axis sections SA and SB in the setting of the first part as the inflow section. The reason is as follows. That is, the inflow section is the tubular structure including the tricuspid valve, and the tricuspid valve is connected to the right atrium so that the inflow section has a slightly complicated shape. Thus, it is desirable that approximation be performed not by a simple tube but by an elliptical tube. On the contrary, in the outflow section, the pulmonary valve is connected to a pulmonary artery, that is, a blood vessel. The blood vessel has a cylindrical shape so that is a reasonable approximation in the method of the embodiment. In addition, even when it is considered in terms of quality of the ultrasonic image, with respect to the inflow section capable of sufficiently securing visibility, the outflow section is unclearly delineated due to a constraint of an acoustic window (a costal region capable of causing the ultrasonic wave to pass therethrough without being covered by a lung). The short-axis image notably receives such influence as in the related art, and thus, to visually confirm a myocardial boundary of the outflow section is significantly difficult. With respect to this, the inventors have found out that the myocardial boundary of the outflow section is visually observed in a relatively easy manner in the long-axis image. Thus, both accuracy in approximation, and reduction in time required for the analysis are established by inputting the contour line of the myocardial boundary using one long-axis section.

Figure 8:
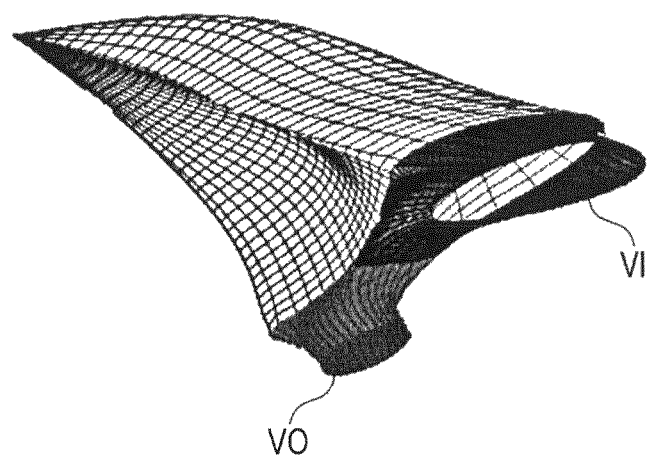
FIG. 8 is a diagram illustrating an example of a three-dimensional shape of a first part VI and a three-dimensional shape of a second part VO to be set onto volume data.

As results of the processes in Steps S2 and S3, for example, as illustrated in FIG. 8, the three-dimensional shape of the first part VI and the three-dimensional shape of the second part VO are respectively set onto the volume data.

Incidentally, the contour line of the myocardial region may be automatically estimated by, for example, the image processing method disclosed in Non Patent Literature 1, similarly to the first setting function 290. In addition, there is no problem even when the order of the setting process of the first part in Step S2 as the previous stage and the setting process of the second part in this Step S3 is reversed.

[Setting of Ventricle Three-Dimensional Myocardial Shape: Step S4]

Figure 9:
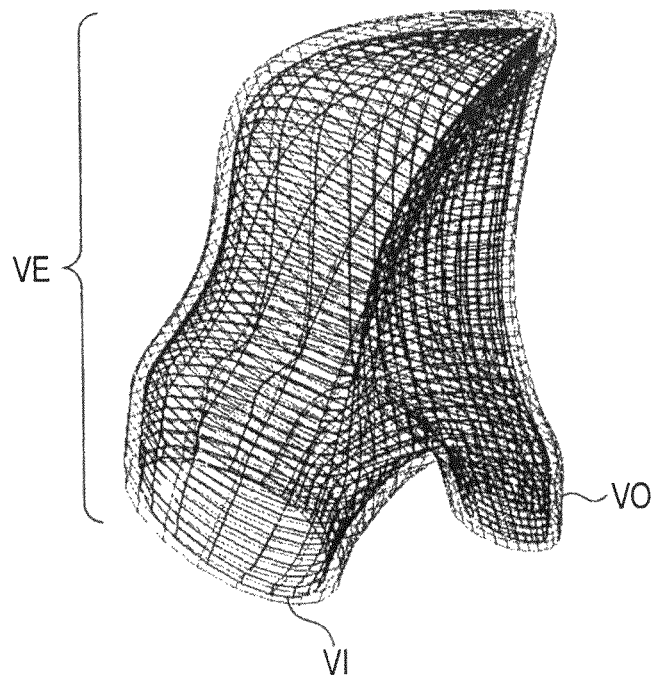
FIG. 9 is a diagram illustrating an example of a three-dimensional myocardial shape VE of a ventricle including the three-dimensional shape of the first part VI and the three-dimensional shape of the second part VO.

The ventricle shape setting function 294 sets the ventricle three-dimensional myocardial shape including the first part and the second part to the volume data using the three-dimensional shape of the first part and the three-dimensional shape of the second part which are approximated. As a result, for example, as illustrated in FIG. 9, the ventricle three-dimensional myocardial shape VE including the three-dimensional shape of the first part VI and the three-dimensional shape of the second part VO is set (or extracted).

Incidentally, in the embodiment, the elliptical shape and the circular shape illustrated in FIG. 10A are deformed in accordance with the shape of the ventricle on the sectional image linked to the ventricle as illustrated in FIG. 10B so as to cause the respective three-dimensional shapes of the inflow section and the outflow section are smoothly connected to each other. However, the present embodiment is not bound to such an example, and, for example, it may be configured such that any one of the inflow section and the outflow section is only deformed on the sectional image linked to the ventricle, and in addition, the approximated three-dimensional shapes of the inflow section and the outflow section are directly used without being deformed so as to be linked to the ventricle.

[Myocardium Tracking according to Pattern Matching: Step S5]

The tracking processing function 296 tracks the ventricle three-dimensional myocardial shape by having the ventricle three-dimensional myocardial shape set in the predetermined temporal phase as the initial shape and performing the pattern matching process, for example, along a time sequence for the volume data corresponding to other respective temporal phases. Accordingly, the ventricle three-dimensional myocardial shape is set in each volume data corresponding to each of the plurality of temporal phases, and further, the velocity distribution image for each temporal phase is generated.

In addition, the tracking processing function 296 tracks the axis of the first part and the axis of the second part by performing the pattern matching process, for example, along the time sequence for the volume data corresponding to other respective temporal phases (or, the volume data corresponding to a desired number of temporal phases) using the axis of the first part and the axis of the second part in the predetermined temporal phase, if necessary. Accordingly, the axis of the first part and the axis of the second part are set in each volume data corresponding to each of the plurality of temporal phases. It may be configured such that the ventricle three-dimensional myocardial shape is set to the volume data in each of the temporal phases by performing the above-described processes in Steps S2 and S3 using the axis of the first part and the axis of the second part in each of the temporal phases set in such a manner.

[Generation and Display of Three-Dimensional Image Representing Ventricle Three-Dimensional Myocardial Shape: Step S6]

The image processing circuitry 28 generates the three-dimensional image representing the ventricle three-dimensional myocardial shape including the first part and the second part by performing, for example, the volume rendering using each volume data to which the ventricle three-dimensional myocardial shape is set. Alternatively, the image processing circuitry 28 cuts the heart into an arbitrary section and generates a sectional image in which boundary lines at which the three-dimensional myocardial boundary intersect each other are imaged by performing a multi-planar reformatting (MPR) process using each volume data to which the ventricle three-dimensional myocardial shape is set. The generated image is subjected to a predetermined processing in the display processing circuitry 30, and then, is displayed on the monitor 14 in a predetermined form.

In addition, the motion information generating function 298 generates the motion information in each position of the myocardium using the generated velocity distribution image in each of the temporal phases. The image processing circuitry 28 generates a motion information image in which, for example, the strain or the like of the ventricle this myocardial region in each of the temporal phases is visualized using the generated motion information in each position of the myocardium. The generated image is subjected to a predetermined processing in the display processing circuitry 30, and then, is displayed on the monitor 14 in a predetermined form.

MODIFIED EXAMPLE 1

In the embodiment, the ventricle three-dimensional myocardial shape including the first part and the second part is set to the volume data using the three-dimensional shapes of the first part and the second part which are approximated. However, the present embodiment is not bound to such an example, and may use information in relation to a shape or the like of the ventricle if the information is provided in advance. To be specific, in a case where there is a three-dimensional image approximating the ventricle by a method of the related art or the like, the ventricle shape setting function 294 may be configured to generate the myocardial boundaries of the inflow section and the outflow section of the ventricle by deforming three-dimensional images of a first part and a second part such that the ventricle and the first part, and the ventricle and the second part are mutually connected to each other smoothly. In addition, the ventricle shape setting function 294 may be configured to use not only the three-dimensional image but also image information. The information in relation to the shape or the like of the ventricle is stored in, for example, the storage circuitry 32 or a storage apparatus on the network and can be acquired at a predetermined timing.

MODIFIED EXAMPLE 2

In the embodiment, a case in which the two long-axis sections SA and SB are used in the setting of the first part and the long-axis section SC, different from the long-axis sections SA and SB, is used in the setting of the second part when setting the contour line of the myocardial region is exemplified. However, the present embodiment is not bound to such an example, and, for example, may set the long-axis section SC to be the common (same) section with the long-axis section SA or SB. In other words, in a case where the second part is present on the long-axis section SA or SB, the setting of the second part may be performed using the long-axis section SA or SB having the second part.

Figure 11:
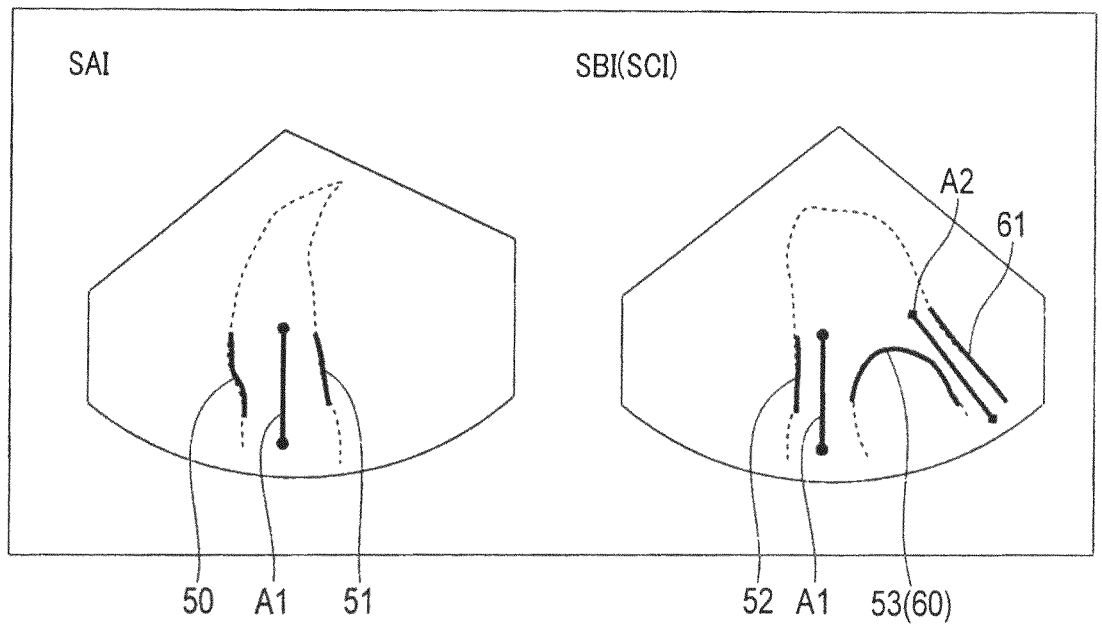
FIG. 11 is a diagram illustrating a modified example of a long-axis sectional image used for setting contour lines 50, 51, 52 and 53 in the first part, and contour lines 60 and 61 of the myocardial region in the second part.

FIG. 11 is a diagram exemplifying a setting screen of the contour line of the myocardial region in a case where the long-axis section SB, which is used to set the contour line of the myocardial region of the first part, and the long-axis section SC, which is used to set the contour line of the myocardial region of the second part, are set to be the same. As illustrated in FIG. 11, according to the present modified example, it is possible to provide two sectional images for setting both the contour line of the myocardial region of the first part and the contour line of the myocardial region of the second part. Accordingly, it is possible to further simplify a user operation as compared to the case of setting the respective contour lines using the three long-axis sectional images.

(Effect)

According to the ultrasonic diagnostic apparatus described above, the contour lines are input using two sections regarding the inflow section having a slightly complicated shape in the long-axis sectional image having relatively easy visibility, regarding the outflow section, and an elliptic cylinder is approximated using the contour lines. On the other hand, the contour line is input using one section regarding the outflow section having a simple shape and difficult visibility due to the blood vessel. Then, the ventricle three-dimensional myocardial shape including the first part and the second part is set to the volume data using the three-dimensional shape of the first part and the three-dimensional shape of the second part which are approximated. Accordingly, the user can easily perform the setting of the myocardial boundary regarding the ventricle with high accuracy. In addition, since the accuracy in the setting of the myocardial boundary is improved, it is possible to reduce the time required for the analysis and the diagnosis, and it is possible to improve the accuracy in the analysis and the diagnosis. Further, it is possible to achieve both the reduction of the time required for the analysis and the diagnosis, and the improvement of the accuracy in the analysis and the diagnosis.

The above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in a memory 5m. In this case, the processing circuitry reads programs incorporated in circuitry and executes the programs to realize predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

Incidentally, the present embodiment is not limited to the above-described embodiment, and components can be modified and embodied in the execution stage within a scope of not departing from a gist of the embodiment. In addition, it is possible to form various types of embodiments by suitably combining a plurality of the components disclosed in the above-described embodiment. For example, some components may be removed from the entire component illustrated in the embodiment. Further, components may be suitably combined across different embodiments. Specific modified examples are as follows, for example.

(1) It is possible to implement the ultrasonic diagnostic apparatus according to the above-described embodiment and the respective modified examples by, for example, using a general-purpose computer apparatus as a basic hardware. In other words, it is possible to implement the function of each unit described above by causing a processor mounted to the above-described computer apparatus to execute a program. At this time, the ultrasonic diagnostic apparatus may be implemented by installing the above-described program to the computer apparatus in advance, and may be implemented by causing the program to be stored in a storage medium such as CD-ROM or distributing the program via a network, and suitably installing the program to the computer apparatus. In addition, the above-described storage unit can be implemented by suitably using a memory, a hard disk, or a storage medium such as CD-R, CD-RW, DVD-RAM or DVD-R, which is built in or externally attached to the above-described computer apparatus.

(2) In the above-described embodiment, the description has been made regarding a case, as the typical example, in which the three-dimensional myocardial shape is set to the volume data in the initial temporal phase in the TTI method. However, the present invention is not bound to such an example, and may be applicable in any type of imaging methods as long as there is a need for setting a three-dimensional myocardial shape to volume data.

(3) In the above-described embodiment, the description has been made exemplifying the ventricle region as the target of setting the three-dimensional myocardial shape. However, the present invention is not bound to such an example, and may be applied to the right atrium or the left atrium.

In addition, it is possible to form various types of inventions by suitably combining a plurality of the components disclosed in the above-described embodiment. For example, some components may be removed from the entire component illustrated in the embodiment. Further, components may be suitably combined across different embodiments.

The invention claimed is:

1. A medical diagnostic apparatus, comprising:
a scanner to scan a three-dimensional region and acquire three-dimensional volume data of the three-dimensional region; and
processing circuitry configured to
generate a three-dimensional shape of a first part for a blood inflow path to a cardiac chamber, the first part being approximated using a first form and based on a contour of the first part in a plurality of first sectional images generated from the three-dimensional volume data, the plurality of first sectional images intersecting each other along an extending direction of the first part in which blood flows;
generate a three-dimensional shape of a second part for a blood outflow path from the cardiac chamber, the second part being approximated using a second form different from the first form and based on a contour of the second part in at least one second sectional image generated from the three-dimensional volume data, the at least one second sectional image being taken along an extending direction of the second part in which blood flows;
generate a three-dimensional shape of the cardiac chamber including the three-dimensional shapes of the first part and the second part by using the generated three-dimensional shape of the first part and the generated three-dimensional shape of the second part;
perform a rendering process using the three-dimensional shape of the cardiac chamber including the three-dimensional shapes of the first part and the second part, and generate a three-dimensional image representing at least part of a heart including the first part, the second part, and the cardiac chamber; and
control a display to display the three-dimensional image.

2. The medical diagnostic apparatus according to claim 1, wherein the processing circuitry is further configured to
set a contour line of at least a part of a myocardial region of the first part using at least two or more of the first sectional images taken along the extending direction of the first part;
approximate the contour of the first part on a plurality of third sections intersecting an axis along the extending direction of the first part by setting an ellipse on each third section based on each position through which the contour line passes in each of the plurality of third sections; and
acquire the three-dimensional shape of the first part by interpolating a plurality of the ellipses.

3. The apparatus according to claim, wherein the processing circuitry is further configured to set a contour line of at least a part of a myocardial region of the second part using the second sectional image taken along the extending direction of the second part;

approximate the contour of the second part on a plurality of fourth sections intersecting an axis along the extending direction of the second part by setting a circle on each fourth section based on each position through which the contour line passes in each of the plurality of fourth sections; and acquire the three-dimensional shape of the second part by interpolating a plurality of the circles.

4. The apparatus according to claim 1, wherein the processing circuitry is further configured to generate a three-dimensional image representing a three-dimensional image of a ventricle including the first part and the second part further using information in relation to the cardiac chamber, which is prepared in advance.

5. The apparatus according to claim 1, wherein the second sectional image along the extending direction of the second part is a same section as any one of the plurality of first sectional images along the extending direction of the first part.

6. The apparatus according to claim 1, wherein the processing circuitry is further configured to track an axis along the extending direction of the first part and an axis along the extending direction of the second part in volume data in at least another temporal phase using an axis along the extending direction of the first part and an axis along the extending direction of the second part in a predetermined temporal phase;

set the first part using the plurality of first sectional images generated from the volume data along the extending direction of the tracked first part with respect to the volume data of the at least another temporal phase;

generate a three-dimensional shape of the first part approximated based on a contour line of at least a part of a myocardial region of the set first part;

set the second part using the at least one second sectional image generated from the volume data along the extending direction of the tracked second part with respect to the volume data of the at least another temporal phase;

generate a three-dimensional shape of the second part approximated based on a contour line of at least a part of a myocardial region of the set second part; and generate the three-dimensional image representing the three-dimensional myocardial shape of the ventricle including the first part and the second part using the three-dimensional shape of the first part and the three-dimensional shape of the second part in the at least another temporal phase.

7. The apparatus according to claim 1, wherein the cardiac chamber is a right ventricle, the first part is a tubular structure including a tricuspid valve, and the second part is a tubular structure including a pulmonary valve.

8. The medical diagnostic apparatus according to claim 7 wherein the processing circuitry is further configured to receive an input from a user for the contour of the first part and the contour of the second part.

9. The apparatus according to claim 1, wherein the cardiac chamber is a ventricle, the first part corresponds to a blood inflow path of the ventricle, and the second part corresponds to a blood outflow path from the ventricle.

10. The apparatus according to claim 1, wherein the cardiac chamber is an atrium, the first part corresponds to a blood outflow path from the atrium, and the second part corresponds to a blood inflow path to the atrium.

11. The medical diagnostic apparatus according to claim 1, wherein a number of the at least one second sectional image is less than a number of the plurality of first sectional images.

12. The medical diagnostic apparatus according to claim 1, wherein the first form is elliptical and the second form is circular.

13. A medical diagnostic apparatus, comprising:
processing circuitry configured to
generate a three-dimensional shape representing a blood inflow path to a right ventricle by approximation using a first form and based on a contour of the blood inflow path in a plurality of first sectional images generated from three-dimensional volume data of at least part of a heart, the plurality of first sectional images intersecting each other along an extending direction of the blood inflow path in which blood flows:

generate a three-dimensional shape representing a blood outflow path from the right ventricle by approximation using a second form different from the first form and based on a contour of the blood outflow path in at least one second sectional image generated from the three-dimensional volume data, the at least one second sectional image being taken along an extending direction of the blood outflow path in which blood flows:

perform a rendering process using the three-dimensional shape representing the blood inflow path and the three-dimensional shape representing the blood outflow path, and generate a three-dimensional image of said at least part of the heart including the blood inflow path, the blood outflow path, and the right ventricle; and control a display to display the three-dimensional image.

14. The apparatus according to claim 13, wherein a number of the at least one second sectional image is less than a number of the plurality of first sectional images.

15. A medical image processing apparatus, comprising:
processing circuitry configured to
generate a three-dimensional shape of a first part for a blood inflow path to a cardiac chamber, the first part being approximated using a first form and based on a contour of the first part in each of a plurality of first sectional images, which are generated from volume data of at least a part of a heart, the first sectional images intersecting each other along an extending direction of the first part in which blood flows:

generate a three-dimensional shape of a second part for a blood outflow path from the cardiac chamber, the second part being approximated using a second form different from the first form and based on a contour of the second part in at least one second sectional image that is generated from the volume data of at least the part of the heart, the at least one second sectional image being taken along an extending direction of the second part in which blood flows:

generate a three-dimensional shape of the cardiac chamber including the three-dimensional shapes of the first part and the second part by using the generated three-dimensional shape of the first part and the generated three-dimensional shape of the second part;

perform a rendering process using the three-dimensional shape of the cardiac chamber including the three-dimensional shapes of the first part and the second part, and generate a three-dimensional image representing at least a part of a heart including the first part, the second part and the cardiac chamber; and control a display to display the three-dimensional image.

16. The medical diagnostic apparatus according to claim 13, wherein the first form is elliptical and the second form is circular.

17. The medical image processing apparatus according to claim 15, wherein a number of the at least one second sectional image is less than a number of the plurality of first sectional images.

18. The medical image processing apparatus according to claim 15, wherein the first form is elliptical and the second form is circular.

19. A medical image processing apparatus, comprising: processing circuitry configured to generate a three-dimensional shape representing a blood inflow path to a right ventricle by approximation using a first form and based on a contour of the blood inflow path in a plurality of first sectional images generated from three-dimensional volume data of at least part of a heart, the plurality of first sectional images intersecting each other along an extending direction of the blood inflow path in which blood flows;

generate a three-dimensional shape representing a blood outflow path from the right ventricle by approximation using a second form different from the first form and based on a contour of the blood outflow path in at least one second sectional image generated from the three-dimensional volume data, the at least one second sectional image being taken along an extending direction of the blood outflow path in which blood flows:

perform a rendering process using the three-dimensional shape representing the blood inflow path and the three-dimensional shape representing the blood outflow path, and generate a three-dimensional image of said at least part of the heart including the blood inflow path, the blood outflow path, and the right ventricle; and control a display to display the three-dimensional image.

20. The apparatus according to claim 19, wherein a number of the at least one second sectional image is less than a number of the plurality of first sectional images.

21. The medical image processing apparatus according to claim 19, wherein the first form is elliptical and the second form is circular.

22. A medical image processing method, comprising:

generating a three-dimensional shape of a first part for a blood inflow path to a cardiac chamber, the first part being approximated using a first form and based on a contour of the first part in a plurality of first sectional images, which are generated from volume data of at least a part of a heart, the first sectional images intersecting each other along an extending direction of the first part in which blood flows, the sectional images concerning with a three-dimensional region;

generating a three-dimensional shape of a second part for a blood outflow path from the cardiac chamber, the second part being estimated using a second form different from the first form and based on a contour of the second part in at least one second sectional image that is generated from the volume data of at least the part of the heart, the at least one second sectional image being taken along an extending direction of the second part in which blood flows;

generating a three-dimensional shape of the cardiac chamber including the three-dimensional shapes of the first part and the second part by using the generated three-dimensional shape of the first part and the generated three-dimensional shape of the second part;

performing a rendering process using the three-dimensional shape of the cardiac chamber including the three-dimensional shapes of the first part and the second part, and generate a three-dimensional image representing at least part of a heart including the first part, the second part and the cardiac chamber; and controlling a display to display the three-dimensional image.

23. The medical image processing method according to claim 22, wherein a number of the at least one second sectional image is less than a number of the plurality of first sectional images.

24. The medical image processing method according to claim 22, wherein the first form is elliptical and the second form is circular.

* * * * *